(12) United States Patent
Vainshelboim et al.

(10) Patent No.: US 6,592,632 B2
(45) Date of Patent: Jul. 15, 2003

(54) SEMI-PERMANENT HAIR DYEING SYSTEM USING SOLUBLE VAT DYES

(75) Inventors: Alex Vainshelboim, Maple Grove, MN (US); Peter Matravers, Plymouth, MN (US)

(73) Assignee: Aveda Corporation, Blaine, MN (US)

( * ) Notice: Subject to any disclaimer, the term of this patent is extended or adjusted under 35 U.S.C. 154(b) by 0 days.

(21) Appl. No.: 09/867,278

(22) Filed: May 29, 2001

(65) Prior Publication Data

US 2003/0074745 A1 Apr. 24, 2003

(51) Int. Cl.⁷ .................................................. A61K 7/13
(52) U.S. Cl. ........................ 8/405; 8/406; 8/407; 8/412; 8/453
(58) Field of Search ............................ 8/405, 406, 453, 8/407, 412

(56) References Cited

U.S. PATENT DOCUMENTS 5,364,415 A * 11/1994 Lewis ............................ 8/406
5,478,359 A * 12/1995 LaGrange et al. ............. 8/412

* cited by examiner

*Primary Examiner*—Mark Kopec
*Assistant Examiner*—Eisa Elhilo
(74) *Attorney, Agent, or Firm*—Karen A. Lowney, Esq.

(57) ABSTRACT

The invention relates to a semi-permanent dye system comprising at least one solubilized vat dye, an aqueous carrier, and substantially no chemical oxidant.

15 Claims, No Drawings

SEMI-PERMANENT HAIR DYEING SYSTEM USING SOLUBLE VAT DYES

FIELD OF THE INVENTION

The present invention relates to the field of hair colorants. More specifically, the invention relates to semi-permanent hair coloring systems.

BACKGROUND OF THE INVENTION

There are a number of goals that are routinely considered in the development of a successful hair dye formulation, particularly semi-permanent or permanent dyes. First, the dye should provide a natural looking, durable and an even deposit of color on the hair. To achieve this, the dye must be able to penetrate the cuticle, and not wash out easily over a determined period of time. It is also preferred that the process that is used to achieve this end is not too harsh or damaging to the hair. Also, the color of the dyed hair should remain substantially reproducible between applications.

These goals are not simple to achieve. Depending factors are the class of dyes being used, the formula the dye is in, and process of the dye application. This is particularly difficult with semi-permanent dyes. These dyes usually have a lesser affinity to hair and intended to wash out over time. Nonetheless, they should be expected to remain in the hair for a certain length of time. The semi-permanent dyes do have certain advantages, however, in being able to produce color on the hair simply by cuticle diffusion and do not require the presence of harsh oxidizing agents to develop color.

The permanent dyes are as their name implies, more resistant to the fading process that is associated with semi-permanent dyes. This type of hair coloring system is more complex however, because the dyeing process relies on the use of dye precursors. When on the hair, the dye precursors are converted to colored compounds that constitute the actual dyes that color the hair. The components of a permanent hair dye system are typically a primary intermediate, a coupler, and hydrogen peroxide. The oxidation of the primary intermediate, followed by coupling with the coupler molecule, typically produces chromophore. Although the color produced by this process is long-lasting and can achieve lightening of the hair due to bleaching of the hair shaft by hydrogen peroxide, it is not without its disadvantages. The chemical process of oxidation is usually harsh, and in order to achieve the result in a reasonable period of time must be carried out at a very high pH. Thus, the user of a permanent dyeing system runs the risk of damage to the treated hair. Also, since the chromophore is formed in situ, rather than preexisting, control of the consistency of a shade from one application of dye to the next is always problematic.

Thus, there continues to be a need for a relatively color-fast dye system that does not rely on the use of harsh oxidative processes to develop color on the hair. The present invention now provides such a system.

SUMMARY OF THE INVENTION

The present invention relates to a hair coloring system comprising a coloring-effective amount of a solubilized vat dye, and substantially no chemical oxidant, such as hydrogen peroxide. The coloring system can also confer color to hair in the absence of other coloring agents typically used for this purpose, for example, nitrophenols, aminophenols or phenylenediamines. The invention also provides a method for durably coloring the hair using solubilized vat dyes, in the absence of any added chemical oxidant.

DETAILED DESCRIPTION OF THE INVENTION

The compounds known as vat dyes are well known. They have been used for thousands of years, examples being the naturally occurring indigo and tyrian purple. In modern times, dyes of this type have been made synthetically, and are widely used in the textile industry for dyeing of cloth, both natural and synthetic(see Joseph Rivlin, *The Dyeing of Textile Fibers, Theory and Practice*, Chapter 10, 1992, incorporated herein by reference). These dyes are aromatic compounds containing two or more carbonyl groups that are joined by conjugated double bonds. Unlike their permanent dye precursors, the vat dyes already contain their chromophore, and therefore do not require the presence of an oxidative agent to generate the chromophore on the hair.

The soluble vat dyes are actually a group of dyes by themselves. They are vat dyes already in the reduced soluble form, and have the unique feature that they will not oxidize by merely exposing them to the air. The soluble vat dyes are esters of the leuco vat dyes. In presence of the acid and at the proper temperature, the ester will hydrolyze to yield the leuco acid of the vat dye, which can then be oxidized even by air, as are regular leuco vats, to its insoluble form.

Solubilized vat dyes were originally used for textiles. This is because they offer many advantages:

1. The reduction step is eliminated and there is no need for careful control of the dye-bath during application.
2. The application is easier to follow since there are not large amounts of electrolytes in the dye-bath that may cause a fast-strike.
3. The solubilized vat dyes can be used in a significantly lowered pH and in diverse applications.

Soluble vat dyes have previously been disclosed for use in dyeing hair, but only in combination with a standard per-oxidation system(U.S. Pat. No. 5,364,415). However, to the best of Applicants' knowledge, solubilized vat dyes have never been used alone for the coloring of hair. Surprisingly, it was found that solubilized vat dyes out-perform other classes of dyes in the semi-permanent dye formula. For example, basic and direct dyes normally used in semi-permanent hair colors wash out after a few shampoos. Solubilized vat dyes, however, can last up to 45 shampoos.

In application, the solublized vat dye is easily penetrated into the hair and is then oxidized back to its insoluble form by simple exposure to the air. This oxidation thereby causes the dye to be retained by the hair and thus coloring the hair.

The solublized vat dyes of the invention can be any of the solublized vat dyes that are cosmetically acceptable. Vat dyes as well as solublized vat dyes encompass two chemical classes, namely the indigoids and the anthraquinone derivatives, with a preference for the anthraquinones because of their color fastness. Examples of useful solublized vat dyes include, but are not limited to, CI Solublized Vat Brown 5(CI 73411), CI Solublized Vat Black 1(CI 73671), CI Solublized Vat Red 1(CI 73361), CI Solublized Vat Green 2(CI 59831), CI Solublized Vat Violet 8(CI 73601), CI Solublized Vat Yellow 4(CI 59101), CI Solublized Vat Brown 1(CI 70801), CI Solublized Vat Red 3. The vat dyes are capable of being used alone, as the sole source of color in a dyeing composition, or in combination with another solublized vat dye. The amount of dye used is dependent upon the final shade desired, and is not particularly critical. However, the dyes are ordinarily used in an amount of about 0.5 to about 10% by weight of the composition, and preferably in a range of about 1 to about 5%.

It was discovered that the dye solution penetrates the hair very quickly, sometimes in a matter of seconds, and the color change on the hair can be observed almost immediately. Oxidation of the dyes back to their insoluble, colored, form is achieved in the absence of harsh oxidizing agents, such as hydrogen peroxide. Instead, sufficient oxidation can occur simply by exposure to air; ordinarily, however, it will be desirable to assist the dyeing procedure by exposing the hair to a hair dryer, preferably a blow dryer on a warm setting, for about 10 minutes.

Although the dyeing composition and application may indeed be as simple as described above, ordinarily the composition and methodology will employ additional features to optimize the process and produce an improved color intensity and/or color fastness. For example, a useful additive to the dye solution is one or more antioxidants. The presence of the antioxidant(s) in the formulation aids in solublization of the dye, reducing precipitation of the dye, and ensuring that the dye is in optimum form for penetration and dyeing of the hair. Examples of useful antioxidants are erythorbic acid, sodium sulfite, sodium metabisulfite, and sodium hydrosulfite. When used, the antioxidant will be present in amount of from about 0.5–5% by weight of the composition. A preferred combination is of sodium metabisulfite and erythorbic acid, particularly preferred in a ratio of about 2:1.

An additional factor that may aid in performance is the use of an alcohol in the formulation, namely benzyl alcohol. The alcohol may constitute up to about 90%, or even more, of the composition, taking into account the other necessary components of the product. However, in most cases, the amount of benzyl alcohol used will be about 0.5 to about 5% by weight.

Because the solublized vat dyes are very versatile and applicable, it is possible to combine the vat dyes with other types of semi-permanent hair dyes.

The semi-permanent dye systems of the present invention have many advantages over comparable existing dyes systems. First, the use of the solublized vat dyes avoids the use of harsh oxidants such as hydrogen peroxide, and thus reduces the possibility of hair damage due to the dyeing process so common with other dyes. The colors are also very bright, and easy to match because of its defined chromophore system. The dyes have a great affinity for the hair, and maintain an exceptional level of color-fastness even after many shampoos. The application of the dye system is also very simple, achievable in a simple rinse-off formula, with color development completed by air exposure, preferably coupled with a hair dryer at a moderate heat setting.

The invention will be further understood by reference to the following non-limiting examples.

EXAMPLES

A number of experiments were carried out to determine the effect of different variables on the development of color and color fastness. The following variables were tested for their effect on the formulation and on the dyeing process:

Variables pH:
  Neutral
  Acidic: using citric acid
  Basic: using ammonium hydroxide, aminomethyl propanol (AMP) and NaOH Antioxidants:
  Erythorbic Acid
  Sodium Sulfite
  Sodium Metabisulfite
  Sodium Hydrosulfite
Solvents:
  DI water
  Alcohol (SD alcohol 40-B proof 190)
  Benzyl Alcohol
Hair Used:
  Natural White (Blonde)
  50% gray
  Yak
Electrolytes:
  NaCl (5% solution)
Different Solubilized Vat Dyes:

| Dye Name | Color Index Number |
| --- | --- |
| CI Solubilized Vat Brown 5 | 73411 |
| CI Solubilized Vat Black 1 | 73671 |
| CI Solubilized Vat Red 1 | 73361 |
| CI Solubilized Vat Green 2 | 59831 |
| CI Solubilized Vat Violet 8 | 73601 |
| CI Solubilized Vat Yellow 4 | 59101 |
| CI Solubilized Vat Brown 1 | 70801 |
| CI Solubilized Vat Red 3 | Not published |

General Procedure

The aqueous solution containing vat dye was heated with agitation to about 50° C. The dye and antioxidant (if used) was then added at 60° C. Following approximately 5 minutes of cooling, the pH was adjusted (if applicable). Hair swatches of 50% gray, natural blond and yak (International Hair Importers & Products Inc., NY) were fully saturated with the dye solution and incubated at 40° C. for 20 minutes. The hair was then rinsed with tepid tap water, towel dried and blown dry at a medium setting.

If hair swatches were washed, the hair was saturated with tepid tap water and shampooed using Rosemary Mint Shampoo (Aveda). The hair was then rinsed thoroughly, combed and blown dry on medium setting.

Results

In preparing the solution, the violet dye appeared to go into solution at constant rate, regardless of an antioxidant being added to the dye, or the pH of the solution. When sodium hydrosulfite was used, it did not go into aqueous solution when used in conjunction with erythorbic acid.

The pH was adjusted to around 10 using various bases (ammonium hydroxide, AMP and NaOH). It is important to note that the solubilized vat dyes also work well in acidic conditions, and can therefore be used in a variety of formulas.

When the dye was applied to dry hair, it appeared to absorb the dye solution very quickly and even "wicked" its way up to the base of the hair swatch. An odor was emitted once dye was added to the hair.

Because some precipitation occurred, tests were conducted to determine if the vat dyes were truly in a reduced form. Therefore various antioxidants were used and the hair color intensity appeared to be greatest with the addition of sodium metabisulfite and erythorbic acid, 2:1 respectively. The addition of these two antioxidants also decreased the amount of precipitate that formed in the solution and the dye appeared to go into the aqueous solution at a faster rate. The addition of electrolyte into the solution did not appear to change the precipitation of dye and appeared to decrease color intensity. The addition of SD alcohol in the original dye solution also did not change the volume of precipitate nor alter the hair color intensity, however addition of benzyl alcohol (5%) increased the hair color intensity greatly as well as decreased fading after washing.

Different concentrations of dye were used ranging from 1–10% and it appeared that above a 2% dye solution, the intensity of color did not appear to change significantly. Conditioning hair after rinsing appeared to intensify color of yak hair, but this result was not readily observable in the other trial swatches.

Most fading occurred during the first two shampoos. The color was seen in the shampoo bubbles and was displaced on the towel when dried. Fading was reduced with the addition of benzyl alcohol into the solution.

In conclusion, the most intense and vibrant color along with greatest wash fastness was seen with a solution containing 5% benzyl alcohol, 4% solubilized vat dye, 2% sodium metabisulfite and 1% erythorbic acid and pH being adjusted with ammonium hydroxide.

Data Analysis

On one fading experiment conducted, L, a, and b values were determined with the use of a chromameter (Minolta) and graphed (FIGS. 1 and 2). Swatch label "1" is a reference swatch in which it was dyed and then rinsed with tap water. Swatch "2" was dyed, rinsed and washed 5 times. The solution that the swatches were dyed with was 4% SVD (violet), 2% Sodium metabisulfite, 1% erythorbic acid and water.

L, a, and b Values Before and After 5 Shampoo Cycles

| | L | A | b | | L | a | b |
|---|---|---|---|---|---|---|---|
| 1 | 23.3 | 30.09 | −10.6 | 1 | 24.26 | 32.58 | −10.53 |
| 2 | 23.87 | 28.39 | −9.53 | 2 | 22.21 | 27.51 | −8.79 |
| 3 | 23.85 | 27.92 | −8.7 | 3 | 22.24 | 28.71 | −10 |
| 4 | 23.91 | 27.72 | −8.84 | 4 | 23.91 | 31.25 | −10.38 |
| 5 | 21.87 | 24.02 | −7.31 | 5 | 26.01 | 35.48 | −13.6 |
| 6 | 25.27 | 31.47 | −10.36 | 6 | 26.23 | 36.41 | −13.87 |
| 7 | 25.16 | 31.56 | −10.06 | 7 | 26.32 | 32.66 | −11.48 |
| 8 | 25.22 | 29.17 | −8.64 | 8 | 25.92 | 30.94 | −10.64 |
| 9 | 25.13 | 28.72 | −8.66 | 9 | 24.06 | 28.58 | −9.6 |
| 10 | 22.81 | 26.61 | −8.03 | 10 | 26.04 | 30.19 | −10.32 |
| Averages: | 24.039 | 28.567 | −9.073 | | 24.72 | 31.431 | −10.921 |

The averages were taken and graphed:

| L | a | b |
|---|---|---|
| 24.039 | 28.567 | −9.073 |
| 24.72 | 31.431 | −10.921 |

The solution for the above data consisted of 5% benzyl alcohol, 5% Solublized Vat Dye and water. The pH was adjusted to 10 using ammonium hydroxide.

FORMULAS

Solublized Vat dyes were incorporated into various formulas to determine applicability of the dyes. Some of the formulas are as follows:

Low VOC Indigo Hair Spray

| CTFA Ingredient | Percent | Sequence |
|---|---|---|
| SD Alcohol 40-B 190 Proof | 51.0 | 1 |
| Solublized Vat Dye (SVD) | 4.0 | 1 |
| Erythorbic Acid | 1.5 | 1 |
| Sodium Metabisulfite | 2.5 | 1 |
| Fragrance | 1.0–0.4 | 1 |
| Octylacrylamide/Acrylates/Butylaminoethyl Methacrylate | 0.2 | 3 |
| VA/Crotonates/Vinyl Neodecanoate Copolymer | 4.5 | 3 |
| Panthenol | 005 | 4 |
| Lauramide DEA | 0.05 | 4 |
| Tocopherol | 0.01 | 4 |
| DI Water | Q.S. | 4 |
| Surfactant | 0.1 | 4 |
| AMP | QS | 5 |

Procedure

At STP, Sequence #1 ingredients were added and mixed until homogeneous. Sequence #2 ingredient was then added and mixed in thoroughly. At medium to high speed, Sequence #3 ingredients were mixed in. At medium mixing speed, Sequence #4 ingredients were added to the mixture and stirred until all lumps of powder dissolved. Finally, the pH was adjusted to 9 with Sequence #5.

The product was applied to 4 yak, 4 natural white and 4 50% gray hair swatches, incubated for 10 minutes at 40° C. and dried. One of each type of hair swatch was kept after dying process, one of each was rinsed with tap water after dyeing process, one of each was washed once with Aveda®Rosemary Mint Shampoo after dyeing process, and one of each was washed 5 times after dyeing process.

Results

There was vibrant and level deposition of dye onto the different hair samples. There was not much difference in amount of fading with the "rinsed" samples and "washed one time" samples.

Indigo Black Malva Shampoo

| CTFA Ingredient | Percent | Sequence |
|---|---|---|
| DI Water | Q.S. | 1 |
| Erythorbic Acid | 1.5 | 1 |
| Sodium Metabisulfite | 2.5 | 1 |
| Wild Cherry Bark Extract | 1.00–0.1 | 2 |
| Camellia Oleifera Extract | 1.00–0.1 | 2 |
| Malva Rotundafolia Flower | 1.00–0.1 | 2 |
| Aloe Barbadensis Leaf Extract | 1.00–0.1 | 2 |
| Prunus Dulcis | 1.00–0.1 | 2 |
| Tetrasodium EDTA | 0.05 | 3 |
| Solublized Vat Dye (SVD) | 2.0–5.0 | 4 |
| Ammonium Lauryl Sulfate | 15.0–30.0 | 5 |
| Cocamidopropyl Betaine | 2.0–5.0 | 6 |
| Cocamidopropyl Hydroxysultaine | 2.0–5.0 | 7 |
| Wheat amino acids | 0.1 | 8 |

-continued

Indigo Black Malva Shampoo

| CTFA Ingredient | Percent | Sequence |
|---|---|---|
| Isostearamidopropyl morpholine lactate | 0.5 | 9 |
| Cocamidopropyl PG-dimonium chloride phosphate | 1.0 | 10 |
| Panthenol | 0.1 | 11 |
| Lauramide DEA | 2.0–5.0 | 12 |
| Fragrance | 0.5 | 13 |
| Tocopherol | 0.03 | 13 |
| Citric Acid | 0.05 | 14 |

Mix thoroughly for 20 minutes Sequence #1 ingredients. Place Sequence #2 ingredients into a 5-micron filter bag, placing the filter bag into the water mixture and circulate for 20 minutes. Add Sequence #3 ingredient with slower mixing to avoid foaming. Add slowly Sequence #4 to the mixture until homogeneous. Sequence #5–#12 ingredients should be added in sequential order, insuring that each component is fully dissolved before adding the next one. Premix Sequence #13 ingredients in a separate container and add the mixture slowly to the main container and mix for 30 minutes. Finally, Sequence #14 ingredient can be added and mixed for 30 minutes.

Natural Indigo Shampoo

| CTFA Ingredient | Percent | Sequence |
|---|---|---|
| Deionized Water | 22.75 | 1 |
| Xanthan Gum | 0.75 | 1 |
| Sodium Metabisulfite | 2.5 | 1 |
| Erythorbic Acid | 1.5 | 1 |
| Cocamide DEA | 6.0 | 2 |
| Cocamidopropyl Betaine | 20.0 | 2 |
| Saponins | 10.0 | 2 |
| Benzyl Alcohol | 5.0 | 2 |
| Rosemary Extract | 0.10 | 2 |
| Comfrey Leaf Extract | 0.10 | 2 |
| Horsetail Extract | 0.10 | 2 |
| Matricaria Extract | 0.10 | 2 |
| Decyl Polyglucose | 15.0 | 2 |
| Avocado Oil | 0.10 | 2 |
| Solublized Vat Dye | 5.0 | 3 |
| Citric Acid | Q.S. | 4 |
| Polyquaternium-10 | 10.0 | 5 |
| Acetamide MEA | 1.0 | 5 |

Procedure

The ingredients of sequence #1 were combined at 60 degrees Celsius under moderate stirring for about 20 minutes or until gum and antioxidants were thoroughly dissolved. The temperature was then brought back down to STP for the remainder of the procedure. Slowly, sequence #2 ingredients were added and mixing continued, making sure the polymer was completely dispersed. Sequence #3 ingredients were then mixed in slowly until homogeneous. Sequence #4 ingredient (the vat dye) was then added until mixed thoroughly. The pH was adjusted to 5.5 (±0.2) with Sequence #5. Sequence #6 ingredient was slowly added and mixed until homogeneous. Sequence #7 was then mixed in slowly until batch was homogeneous.

Indigo Hair Conditioner with Tea Tree Oil

| CTFA Ingredient | Percent | Sequence |
|---|---|---|
| Deionized Water | QS | 1 |
| Xanthan Gum | 0.75 | 1 |
| Sodium Metabisulfite | 2.5 | 1 |
| Erythorbic Acid | 1.5 | 1 |
| Methylparaben | 0.2 | 2 |
| Methychloroisothiazolinone and methylisothiazolinone (mix) | 0.1 | 2 |
| Hydrolyzed Whole Wheat Protein | 0.1 | 2 |
| Dicetyldimonium Chloride | 1.0 | 3 |
| Cetearl Alcohol and Ceteareth-20 (mix) | 2.0 | 4 |
| Stearamidopropyl Dimethylamine | 1.35 | 4 |
| Tea Tree Oil | 2.0 | 4 |
| Propylparaben | 0.05 | 4 |
| Benzyl Alcohol | 5.0 | 4 |
| Fragrance | 0.2 | 5 |
| Solublized Vat Dye | 5.0 | 6 |
| Citric Acid | 0.3 | 6 |

The ingredients of sequence #1 were combined at 60° Celsius under moderate stirring for about 20 minutes or until gum and antioxidants were thoroughly dissolved. The temperature was then raised to 78° Celsius. Sequence #2 was then added until a clear uniform solution was obtained. Sequence #3 was added, maintaining thorough mixing and temperature. In a separate mixing container, sequence #4 was mixed and heated to 72° Celsius. At proper temperature, Sequence #4 was added to the main container, maintaining temperature until emulsification was complete. The temperature was then cooled to 40° Celsius with slower mixing. At 40° C., Sequence #5 was added, cooling to 30° Celsius. At 30° Celsius, Sequence #6 was added and cooled to 25° Celsius.

What we claim is:

1. A semi-permanent dye system comprising at least one solubilized vat dye, an aqueous carrier, and no chemical oxidant.

2. The system of claim 1, which further comprises an alcohol.

3. The system of claim 2, in which the alcohol comprises benzyl alcohol.

4. The system of claim 1, which further comprises an antioxidant.

5. The system of claim 4 in which the antioxidant is erythorbic acid, sodium sulfite, sodium metabisulfite, sodium hydrosulfite, or a combination thereof.

6. The system of claim 5 in which the antioxidant comprises a combination of sodium metabilsulfite and erythorbic acid in a ratio of about 2:1.

7. A semi-permanent dye system comprising at least one solubilized vat dye, an aqueous carrier, at least one antioxidant, at least one alcohol, and no chemical oxidant.

8. The system of claim 7 which comprises from about 0.5 to about 10% by weight of vat dye, from about 0.05 to about 5% by weight of antioxidant, and from about 0.5 to about 5% by weight benzyl alcohol.

9. The system of claim 8 in which the antioxidant is selected from the group consisting of erythorbic acid, sodium sulfite, sodium metabisulfite, sodium hydrosulfite, or a combination thereof.

10. The system of claim 9 which comprises from about 1 to about 5% by weight of vat dye, and sodium metabisulfite and erythorbic acid as antioxidant in a ratio of about 2:1.

11. A method of coloring hair which comprises applying to the hair the system of claim 1, and permitting the dye to oxidize on the hair without the use of a chemical oxidizing agent.

12. A method of coloring hair which comprises applying to the hair the system of claim 7, and permitting the dye to oxidize on the hair without the use of a chemical oxidizing agent.

13. A method of coloring hair which comprises applying to the hair the system of claim 8, and permitting the dye to oxidize on the hair without the use of a chemical oxidizing agent.

14. A method of coloring hair which comprises applying to the hair the system of claim 9, and permitting the dye to oxidize on the hair without the use of a chemical oxidizing agent.

15. A method of coloring hair which comprises applying to the hair the system of claim 10, and permitting the dye to oxidize on the hair without the use of a chemical oxidizing agent.

* * * * *